United States Patent
Hasegawa et al.

(10) Patent No.: US 7,374,783 B2
(45) Date of Patent: May 20, 2008

(54) POWDERS COATED WITH SPECIFIC LIPOAMINO ACID COMPOSITION AND COSMETICS CONTAINING THE SAME

(75) Inventors: Yukio Hasegawa, Saitama (JP); Toru Sakurada, Saitama (JP); Taizo Miyoshi, Saitama (JP)

(73) Assignee: Miyoshi Kasei, Inc., Saitama (JP)

( * ) Notice: Subject to any disclaimer, the term of this patent is extended or adjusted under 35 U.S.C. 154(b) by 670 days.

(21) Appl. No.: 10/899,310

(22) Filed: Jul. 27, 2004

(65) Prior Publication Data

US 2006/0024375 A1    Feb. 2, 2006

(51) Int. Cl.
- *A61K 9/14* (2006.01)
- *A61K 9/16* (2006.01)
- *A61K 31/70* (2006.01)
- *A01N 43/04* (2006.01)

(52) U.S. Cl. .................. 424/489; 424/490; 514/45; 514/49

(58) Field of Classification Search ................. 424/489, 424/490; 514/45, 49
See application file for complete search history.

(56) References Cited

FOREIGN PATENT DOCUMENTS

| | | |
|---|---|---|
| JP | 58-72512 | 4/1983 |
| JP | 60-069011 A | 4/1985 |
| JP | 62-087237 A | 4/1987 |
| JP | 1-172312 | 7/1989 |
| JP | 5-58842 | 3/1993 |
| JP | 9-208427 | 8/1997 |
| JP | 11-296515 * | 8/2000 |
| JP | 2000-212041 | 8/2000 |
| WO | WO 94/15580 A1 | 7/1994 |

* cited by examiner

*Primary Examiner*—Johann R. Richter
*Assistant Examiner*—Konata M. George
(74) *Attorney, Agent, or Firm*—Westerman, Hattori, Daniels & Adrian, LLP.

(57) ABSTRACT

There is provided a coated powder having a high skin care effect and a high anti-aging effect. The powder which can be used in cosmetics is coated with a mixture (lipoamino acid composition) comprising N-acyl derivatives (also including the form of a salt) of (1) at least one amino acid selected from proline and hydroxyproline, (2) at least one amino acid selected from alanine, glycine and sarcosine and (3) at least one amino acid selected from aspartic acid and glutamic acid, and at least one selected from fatty acids (and/or metal salts thereof) having a carbon number of at least 12 and at most 22.

13 Claims, No Drawings

US 7,374,783 B2

POWDERS COATED WITH SPECIFIC LIPOAMINO ACID COMPOSITION AND COSMETICS CONTAINING THE SAME

FIELD OF THE INVENTION

The present invention relates to a novel coated powder which can be used in cosmetics and a novel cosmetic containing the same. More specifically, the present invention relates to a coated powder which can be used in cosmetics and which is coated with a mixture (lipoamino acid composition) comprising N-acyl derivatives (also including the form of a salt) of amino acids shown in the following (1) to (3) and at least one selected from fatty acids (and/or metal salts thereof) having a carbon number of at least 12 and at most 22, and cosmetics containing the powder.

(1) at least one amino acid selected from proline and hydroxyproline, (2) at least one amino acid selected from alanine, glycine and sarcosine, and (3) at least one amino acid selected from aspartic acid and glutamic acid.

More specifically, the powders coated with these mixtures (lipoamino acid compositions) are not only good in aesthetic feeling in use, extension and adhesiveness on the skin, and dispersibility, which are properties of ordinary coated powders, but also have a high skin-care effect and a high skin anti-aging effect. Accordingly, cosmetics containing the same are quite useful.

BACKGROUND OF THE INVENTION

In recent years, cosmetics have contained various powders. The types of powders are roughly classified into organic powders and inorganic powders, but recently, the market has seen many composite powders containing both organic and inorganic powders. Effects of cosmetics containing these powders include skin color adjustment, cover up of a blemish, a freckle and the like, adjustment of skin qualities, impartment of a color, impartment of brightness, sebum absorption, improvement of touch, prevention of ultraviolet rays and infrared rays, an anti-inflammatory activity, sedation, a massage effect, an effect of preventing the deterioration of makeup off the skin and the like. Meanwhile, demerits provided by incorporating powders into cosmetics include, mainly in case of inorganic powders, skin irritation caused by a powdery feeling on the skin, physical irritation caused when coated onto the skin, occurrence of chemical catalytic activity of powders and the like, occurrence of dry skin caused by the absorption of sweat or sebum of the skin by powders, a dull color given by wetting of powders with sweat or sebum, and the like.

Cosmetics containing powders include not only makeup products but also skin care products, sunscreen products, shampoos, rinses, hair tonics, hair growth promoters, cleansers, antiperspirants, bath products, and the like. It is proposed that the particulate surface of the powder incorporated into these products is coated with silicone compounds, fluorine compounds, esters, fatty acids, waxes, amino acids, peptides, lecithin, polyolefins, coupling agents, surfactants and organic compounds such as water-soluble polymers in order to maximize the functions of powders and presenting them in cosmetic effects. Among these coating agents, amino acids are one of many components making up the living body, and amino acids obtained by acylating the same, are expected to provide various physiological activities to the skin. The powders coated with the acylated amino acids are deemed to have effects such as improvement of a feeling in use, improvement of an adhesiveness to the skin, impartment of water repellency and water resistance, impartment of oil repellency, improvement of miscibility with oil components, improvement of duration of cosmetic effects, storage stability, dispersibility and UV-screening ability, excellent biocompatibility and the like, and many proposals have been made.

For example, it is reported that a powder coated with an N-acylated amino acid amide such as N-lauroyl-L-glutamic acid-α,γ-di-n-butyl amide has characteristics that it can impart a water repellency and has good skin adhesion,and a smooth aesthetic touch and also has good miscibility with oil components because of a high lipophilicity (refer to, for example, Japanese Patent Kokai Publication JP-A-1-172312 (pp. 3-6, Tables 1 and 2)).

It is reported that a powder coated with N-lauroyl-L-lysine is excellent in spreadability on the skin, primary as well as final aesthetic feeling, and also excellent in makeup duration over the course of time (refer to, for example, JP-A-9-208427 (pp. 3-6, Tables 3 and 4)).

Furthermore, there is a report about a powder that is double-coated with an acylated basic amino acid and a fat (for example, fatty acid) having an acid group (refer to, for example, JP-A-5-58842 (pp. 4-9)) This coated powder shows water repellency, prevents makeup from coming off due to sebum or the like, also improves spreadability of cosmetics on the skin and imparts good touch to the skin.

The present inventors have proposed powders coated with N-acyl-L-glutamic acid, N-acyl-N-methylglycine, N-acyl-N-methyl-β-alanine and salts thereof (refer to, for example, JP-A-58-72512 (pp. 4-6)). Cosmetics containing this powder have a function of protecting the skin, and have excellent adhesion to the skin, touch, and stability.

The present inventors have improved the powders coated with the above N-acylated amino acids, and have reported powders coated with mixtures containing N-acyl derivatives of at least 14 amino acids (refer to, for example, JP-A-2000-212041 (pp. 8-22, FIG. 1)). The powders have quite a smooth touch, and are good in feeling when applied to the skin or the hair and have excellent biocompatibility.

Cosmetics in general have an objective of making the skin clean and beautiful without impairing a physiological activity of healthy skin. Further, people wish to stay beautiful and young forever. Functional cosmetics that realize this hope have been required. To meet these requirements, cosmetics contain components having a skin care effect and components having an anti-aging effect. However, a coated powder that exhibits a good skin care effect, providing a moisturizing function, adjusting skin texture, and providing an anti-aging effect of improving the rough skin, has not been proposed.

SUMMARY OF THE DISCLOSURE

Accordingly, it is an object of the invention to provide a coated powder having a high skin care effect and a high skin anti-aging effect and cosmetics containing the same.

The present inventors have assiduously conducted investigations to solve the foregoing problems, and have consequently found that cosmetics containing a powder coated with a specific lipoamino acid composition are quite excellent in skin care effect and anti-aging effect. This finding has led to the completion of the invention.

That is, a coated powder which can be used in cosmetics according to the invention is characterized in that a powder is coated with a mixture (lipoamino acid composition)

comprising N-acyl derivatives (also including the form of a salt) of amino acids shown in the following (1) to (3) and at least one selected from fatty acids (and/or metal salts thereof) having a carbon number of at least 12 and at most 22:

(1) at least one amino acid selected from proline and hydroxyproline, (2) at least one amino acid selected from alanine, glycine and sarcosine, and (3) at least one amino acid selected from aspartic acid and glutamic acid.

In a preferred embodiment, the carbon number of the fatty acid is from 12 to 18.

The N-acyl group of the N-acylamino acid is a saturated or unsaturated alkyl group (alkenyl or the like, which may have a carbon-carbon double bond and/or triple bond in a molecule) or a hydrocarbon group of an alicyclic structure having carbon numbers 8 to 22. A saturated aliphatic carbonoyl group having a carbon number from 12 to 22 is preferable, and more preferably the carbon number is any from 12 to 18. The carboxyl group of the amino acids (1) to (3) is in the free form or in the form of a salt. Examples thereof include salts of metals such as Na, K, Ba, Zn, Ca, Mg, Fe, Zr, Co, Al and Ti, an ammonium salt, onium salts of organic alkanolamines such as monoethanolamine, diethanolamine, triethanolamine, 2-amino-2-methylpropanol, 2-amino-2-methyl-1,3-propanediol and triisopropanolamine. The free form or any of salts of Na, K and a polyvalent metal is preferable. The free form, salts of Na, K, Ca, Mg and Al or a mixture thereof is more preferable.

The amino acids (1) to (3) in the invention exist in nature or are L-isomers obtained from the natural world. Most of amino acids have isomers. In this case, amino acids can also be used in the form of a mixture or a compound so long as they include isomers, namely L-isomers which exist in nature or are obtained from the natural world. For example, when an amino acid contains a D-isomer and an L-isomer, an L-isomer exists in nature. In the invention, such an amino acid in the form of a DL-isomer maybe used so long as it contains an amino acid L-isomer existing in nature. The mixture of the N-acylated amino acids used in the invention may further contain other amino acids, an N-acyl derivative of an isomer of an amino acid other than the above-mentioned, and substances other than an amino acid and its derivatives, so long as the N-acyl derivatives of the amino acids are contained therein. It is advisable that they are contained, unless it impairs the effects of the invention.

The N-acyl derivatives of the amino acids (1) to (3) used in the invention may be independently in the free form or in the form of a salt. When all of the N-acylamino acids take the salt forms, the salt forms constituting the respective N-acylamino acids are independent. All or a part thereof may take the same salt form or different salt forms. The amino acids as the starting materials may be in the form existing in nature (L-isomer except glycine). As stated above, the form of the mixture is available so long as the very form (isomer) is contained as mentioned above. The production route is not particularly limited. Accordingly, products obtained by an extraction method, a synthetic method, and a microbiological production method, and amino acids obtained by various methods such as protein and peptide hydrolysis methods and the like can be used.

The fatty acid and/or its metal salt used in the invention is a compound having a carbon number of at least 12 and at most 22. Specific examples thereof include lauric acid, myristic acid, isomyristic acid, palmitic acid, isopalmitic acid, stearic acid, isostearic acid, oleic acid, myristoleic acid, elaidic acid, linoleic acid, linolenic acid and the like. Fatty acids of coconut oil that are a mixture of fatty acids derived from plant, in particular, coconut palm are also exemplary enumerated. Metals of their metal salts include Na, K, Ba, Be, Ce, Ca, Co, Mg, Fe, Sr, Zn, Zr, Al, Ti and the like. Fatty acids such as lauric acid, myristic acid, palmitic acid, stearic acid, and fatty acids of coconut oil and their salts with Na, K, Ca, Al and Mg are preferable. A fatty acid selected from lauric acid, myristic acid, palmitic acid and stearic acid is more preferable.

The minimum content of each component in the mixture of the N-acylated amino acids (1) to (3) and the fatty acid (and/or its metal salt) used in the invention is 0.5% by weight or more. When the content is less than 0.5% by weight, no synergistic effect is provided. With respect to the contents of the respective components in the preferable mixture in which the high skin care effect and skin anti-aging effect referred to in the invention are satisfactorily exhibited, the N-acyl derivative of the amino acid (1) is from 25 to 70% by weight, the N-acyl derivative of the amino acid (2) is from 5 to 50% by weight, the N-acyl derivative of the amino acid (3) is from 5 to 25% by weight, and the fatty acid (and/or its metal salt) is from 5 to 50% by weight.

Regarding a method for coating the powder, the powder can be coated by any known coating method which has been so far used for improving powders used in cosmetics. Regarding a method for incorporating the powder, the powder can be incorporated by any known method for incorporating a powder or a coated powder which has been so far used for incorporation in cosmetics.

PREFERRED EMBODIMENT OF THE INVENTION

The coated powder of the invention is a powder obtained by coating a part or the whole of a particulate surface of at least a part of powders to be incorporated and used in cosmetics with the mixture (lipoamino acid composition) of the specific acylated amino acid and fatty acid. In the invention, the "lipoamino acid" is a general term of a complex or a compound comprising an amino acid and a lipid. The binding type between an amino acid and a lipid includes non-covalent bonds such as an ionic bond between a basic side chain of an amino acid and a phosphoric acid group of a lipid, a van der Waals bond between a hydrophobic side chain of an amino acid and a lipid, covalent bonds such as an ester bond between a carboxyl group of an amino acid and a hydroxyl group of a lipid (example: 3'-o-lysylphosphatidylglycerol) or between a hydroxyl group of an amino acid and a phosphoric acid group of a lipid (example: phosphatidyl serine), and an amide bond between an amino group of an amino acid and a carboxyl group of a fatty acid. In the invention, the N-acylated amino acid is preferable.

In the invention, the "skin care effect" refers to an effect of providing a moisturizing effect and maintaining smooth skin. Active oxygen generated on the skin by external stimulation with ultraviolet rays, chemical substances, or by drying or the like acts to change the dermis matrix through decrease of collagen, increasing the denaturation of elastin or the like to lose the elasticity of the skin. The "anti-aging effect" refers to an effect of restoring the elasticity of the skin by improving the conditions of the connective tissues.

The coated powder of the invention exhibits maximum effects of the invention when coated with the mixture. The four components constituting the mixture may be coated separately.

The specific lipoamino acid composition used in the invention can be produced by any known method. It can be produced by a method disclosed in, for example, WO 98/09611, WO 99/04757 or JP-A-2000-191426. When it is procured easily, a trade name "SEPIFEEL ONE" marketed as a commercial product by SEPPIC, France can be purchased.

The powder used in the invention is not particularly limited, and any powders that are commonly available in cosmetics may be used. Further, powders for cosmetics which may be developed in the future can also be used. The average particle diameter thereof is preferably from 3,000 μm to 0.001 μm, more preferably from 200 μm to 0.01 μm. The particle diameter of these powders is obtained from an average value measured by observation with an optical microscope or an electron microscope. A particle diameter of particles which are not spherical can be obtained from an average value of a total of a major diameter, a minor diameter, a thickness and the like.

Examples of the inorganic powder include extender pigments such as mica, sericite, talc, kaolin, synthetic mica, muscovite, phlogopite, epidolite, biotite, lithia mica, calcium carbonate, magnesium carbonate, calcium phosphate, alumina, magnesium oxide, aluminum hydroxide, barium sulfate, magnesium sulfate, silicic acid, silicic anhydride, magnesium silicate, aluminum silicate, aluminum magnesium silicate, calcium silicate, barium silicate, strontium silicate, silicon carbide, tungstic acid metal salt, magnesium aluminate, magnesium metasilicate aluminate, chlorohydroxyaluminum, clay, bentonite, zeolite, smectite, hydroxyapatite, ceramic powder, boron nitride and silica; special composite extender pigments such as Excel Mica, Excel Pearl and Powder La Vie sold by Miyoshi Kasei, Inc.; white pigments such as titanium dioxide, zinc oxide and cerium oxide; color pigments such as red iron oxide, yellow iron oxide, black iron oxide, chromium oxide, chromium hydroxide, Prussian blue, ultramarine, inorganic blue pigment, carbon black, lower titanium oxide, mango violet, cobalt violet, laked tar dye and laked natural dye; bright pigments such as bismuth oxychloride, mica titanium, fish scale guanine, a powder obtained by coating synthetic mica with titanium dioxide, a powder obtained by coating silica flakes with titanium dioxide as sold under a trade name "Metashine" by Nippon Sheet Glass Co., Ltd., a powder obtained by coating alumina flakes with tin oxide and titanium dioxide, a powder obtained by coating aluminum flakes with titanium dioxide, a powder obtained by coating copper flakes with silica as sold by Eckart, U.S.A., a powder obtained by coating bronze flakes with silica and a powder obtained by coating aluminum flakes with silica; finely divided powders having an average particle diameter of less than 0.1 μm, such as finely divided titanium dioxide, finely divided zinc oxide, finely divided iron oxide and finely divided cerium oxide; and powders having a special particulate shape, such as butterfly-shaped barium sulfate, petal-shaped zinc oxide and nylon fibers having a major diameter of several millimeters; and other powders such as a luminous powder sold under a trade name "Luminova Series" by Mitsui & Co., Ltd., an aluminum powder, a stainless powder, a tourmaline powder and an amber powder.

Examples of organic powder include a wool powder, a polyamide powder, a polyester powder, a polyethylene powder, a polypropylene powder, a polystyrene powder, a polyurethane powder, a benzoguanamine powder, a polymethylbenzoguanamine powder, a tetrafluoroethylene powder, a polymethyl methacrylate powder, a cellulose powder, a silk powder, a silicone powder, a silicone rubber powder, a styrene.acrylic copolymer, a divinylbenzene.styrene copolymer, synthetic resin powders such as a vinyl resin, a urea resin, a phenol resin, a fluoro resin, a silicon resin, an acrylic resin, a melamine resin, an epoxy resin and a polycarbonate resin, a fine crystalline fibrous powder, a starch powder, an acylated lysine powder, a long-chain alkyl phosphate metallic salt powder, a metal soap powder, CI Pigment Yellow, CI Pigment Orange and the like. Examples of tar dye include Red No. 3, Red No. 10, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206 and Orange No. 207. Examples of natural dye include powders of carmine, laccaic acid, carthamine, brazilin, crosin and the like.

With respect to the form of the powder used, the form which is ordinarily incorporated in cosmetics, such as a mixture, a composite, or an adhered powder can be used. For example, these powders can be used by being complexed or doped as required. Examples thereof include a powder obtained by coating an inorganic color pigment such as red iron oxide with silicic anhydride, a powder obtained by coating nylon with a white pigment, a powder obtained by coating an extender pigment with a finely divided white pigment and the like.

The type and the content of the powder used in cosmetics are properly selected depending on the type, the purpose, the form and the like of cosmetics. For example, at least one of the above-listed powders is selected. Powders which may be developed in the future can obviously be used. The type, the use amount and the use method thereof can be selected by any known methods for using powders, which are available in cosmetics and also methods, which will be developed in the future.

In the invention, the amount of the specific lipoamino acid composition coated on the powder varies with the particle diameter, the specific surface area of the powder, the surface condition of the powder, and the like. It is from 0.1 to 30%, especially preferably from 1.0 to 10% based on the powder. When the amount is less than 0.1%, desirable effects are not obtained. When the composition is coated in an amount of more than 30%, the function of the powder is impaired, and it is also uneconomical.

When the powder is coated with the specific lipoamino acid composition, it is advisable to use any known method. For example, a water-soluble salt of the specific lipoamino acid composition is dissolved in water, and the powder is added to the resulting solution, and dispersed well therein. The dispersion is dehydrated, filtered, washed, and then dried. A water-insoluble lipoamino acid composition is dissolved in an appropriate solvent such as methyl ethyl ketone or ethyl acetate, and the solution is mixed with the powder. The solvent is distilled off, and the residue is dried to be able to obtain a coated powder. However, the invention is not limited to such coating methods.

For improving an affinity for a coating agent or bindability therewith, the surface-treated powder may be coated with an oxide or a hydroxide of at least one of aluminum, calcium, magnesium, cerium, silicon, zirconium, titanium, zinc, iron, cobalt, manganese, nickel, and tin. Further, the powder may be previously coated, for providing a synergistic effect of coating, with a silicone compound, an acylated amino acid, an acylated peptide, a fatty acid, a metallic soap, a fluorine compound, lecithin, a polyalkylene, a silane coupling agent, ceramide, a dextrin fatty acid ester, inulin fatty acid ester or the like.

The specific lipoamino acid composition as the coating agent of the invention is also quite useful as the surface active agent of the A layer or the B layer proposed by the present inventors as described in JP-A-2001-72527 or 2002-80748.

The amount of the thus-obtained coated powders which are incorporated into cosmetics is optionally determined depending on qualities of cosmetics. It is from 0.01 to 100% by weight based on the total composition. One or more of these coated powders can be incorporated as required.

In the cosmetics of the invention, the coated powders of the invention may be applied to at least a part of powders to be incorporated and used therein, particularly, higher incorporation rate is preferable.

Examples of the cosmetics containing the powders coated with the specific lipoamino acid composition of the invention include makeup products such as a powder foundation, a liquid foundation, an oil foundation, a stick foundation, a pressed powder, a face powder, a lipstick, a lip gloss, a rouge, an eye shadow, an eye brow, an eye liner, a mascara, an aqueous nail enamel, an oil nail enamel, an emulsion nail enamel, an enamel top coat and an enamel base coat, skin products such as an emollient cream, a cold cream, a whitening cream, an emulsion, a cosmetic lotion, a beauty lotion, a carmine lotion, a slimming product, a liquid face wash, a face wash foam, a face wash cream, a face wash powder, a makeup cleansing, a body gloss and a shaving product, hair products such as a hair gloss, a hair cream, a hair shampoo, a hair rinse, a hair color and a hair brushing product, an anti-sunburn cream, a sunburn cream, a sedative care product after sunburn, an emulsion, a soap, a bath agent, a scent, and the like.

The cosmetics containing the powders coated with the specific lipoamino acid composition used in the invention can properly contain a pigment dispersant, oil, a surfactant, a UV absorber, an antiseptic, an antioxidant, a film-forming agent, a humectant, a thickener, a dye, a pigment, a perfume and the like which are used in ordinary cosmetics or the like as stated earlier, unless it impairs the effects of the invention.

EXAMPLES

The invention is described in detail below by referring to Examples and Comparative Examples. These do not limit the invention in any way.

Example 1

Preparation of Coating Agents 1-1 Preparation of Coating Agent A 45.5 g of lauroylproline, 30.5 g of N-lauroylglycine, 5.5 g of N-lauroylglutamic acid and 18.5 g of palmitic acid were charged into a glass beaker heated to 65° C., dissolved by mixing, and then cooled to obtain a solid matter. This solid matter was designated coating agent A.

1-2 Preparation of Coating Agent B 35 g of dipalmitoylhydroxyproline, 35 g of N-myristoylalanine sodium salt, 7.5 g of N-palmitoylaspartic acid, 22.5 g of myristic acid and 50 cc of water were charged into a glass beaker, and dissolved by being mixed at 50° C., and then cooled to obtain a paste. This was designated coating agent B.

1-3 Preparation of Coating Agent C 160.0 g of palmitoylproline, 130 g of palmitoylsarcosine sodium salt, 38 g of potassium palmitoylglutamate, 72 g of magnesium stearate and 200 cc of water were charged into a glass beaker, dissolved by being mixed at 75° C., and then cooled to obtain a paste. This was designated coating agent C.

1-4 Preparation of Coating Agent D

A product under a trade name "SEPIFEEL ONE" marketed in SEPPIC, France was used as coating agent D. The composition was 44.5% by weight of palmitoylproline, 12.5% by weight of palmitoylsarcosine sodium salt, 8.5% by weight of magnesium palmitoylglutamate and 34.5% by weight of palmitic acid.

Example 2

Production of Coated Powder-1

100 g of a powder to be coated and 3 g of coating agent A were charged into a laboratory mixer fitted with a jacket, and stirred for 30 minutes while keeping the inside temperature of the mixture at 60° C. to obtain a coated powder. As the powder to be coated, four types of powders, mica MJ-V (Merck Japan K.K.), Powder La Vie (Miyoshi Kasei, Inc.), mica titanium TIMIRON SUPER RED (Merck Japan K.K.) and Excel Mica JP-2 (Miyoshi Kasei, Inc.) were used, and were coated respectively by the foregoing method to obtain four types of coated powders.

Example 3

Production of Coated Powder-2

100 g of synthetic fluorine phlogopite PDM-9WB (Topy Kogyo K.K.) was charged into a kneader mixer, and mixed with 6 g of coating agent B and 50 g of hot water of 60° C. for 30 minutes. The mixture was then dried in an oven at 105° C. for 12 hours, and passed through a mill to obtain a coated powder.

Example 4

Production of Coated Powder-3

3 kg of finely divided titanium oxide TTO-S-3 (Ishihara Sangyo Kaisha Ltd.) and 350 g of coating agent C were charged into a 20-liter heater Henschel (Mitsui Mining Co., Ltd.), and stirred for 20 minutes for coating. This mixture was pulverized with a jet mill 100 AFG (Germany: ALPINE), and then dried in an oven at 105° C. for 7 hours to obtain a coated powder.

Example 5

Production of Coated Powder-4

100 g of silica beads P-1500 (Catalysts & Chemicals Industries Co., Ltd. (CCIC)) was charged into a kneader mixer, and mixed with 8 g of coating agent D and 60 g of hot water of 80° C. for 30 minutes. The mixture was then dried in an oven at 105° C. for 15 hours, and passed through a mill to obtain a coated powder. In the same manner, with respect to sericite FSE (Sanshin Mining Ind. CO., Ltd.), talc JA-46R (Asada Milling K.K.), titanium dioxide CR-50 (Ishihara Sangyo Kaisha Ltd.), Yellow LL-100P (Titanium Kogyo K.K.), Red R-516P (Titanium Kogyo K.K.) and Black BL-100P (Titan Kogyo K.K.), 100 g of each powder was coated with 3 g of a coating agent.

Comparative Example 1

Production of Coated Powder-5

Synthetic fluorine phlogopite was surface treated by the method described in (a) of Example 1 in JP-B-1-50202 to obtain aluminum N-myristoyl-L-glutamate-treated powder (amount of surface treatment 3% by weight).

Comparative Example 2

Production of Coated Powder-6

Synthetic fluorine phlogopite PDM-9WB was coated with N-lauroyllysine by the method of Production Example 1 described in JP-A-8-67609. The coating method is described below. 5 g of N-lauroyllysine was dissolved in 500 g of water adjusted to pH of approximately 12 by dissolving 0.2 g of sodium hydroxide. 95 g of the powder was dispersed therein to obtain a slurry. 2.5 g of calcium chloride was added thereto for neutralization to approximately a neutral region to precipitate N-lauroyllysine calcium salt. The salt formed during the neutralization was removed by being washed with water, and the residue was dried at 100° C. for 2 hours to obtain an N-lauroyllysine-treated synthetic fluorine phlogopite.

Comparative Example 3

Production of Coated Powder-7

A powder was coated with N-lauroyllysine and palmitic acid by the method of Example 1 described in JP-A-5-58842. The coating method is described below. 100 g of the powder was charged into a kneader mixer, a solution of 100 g of calcium chloride in 5,000 g of ethanol prepared previously was added thereto, and they were mixed at room temperature for 2 hours with stirring. Subsequently, the mixture was filtered, and washed with water to remove calcium chloride. The residue was then dried to obtain an N-lauroyllysine-coated powder. 100 g of the resulting coated powder was charged into a kneader mixer. A solution of 1.5 g of palmitic acid in 50 g of hexane was added thereto, and they were mixed at 60° C. for 30 minutes. Subsequently, hexane was distilled off at 60° C. under reduced pressure, and the residue was dried at 100° C. for 1 hour to obtain a powder coated with N-lauroyllysine and palmitic acid. The powders to be coated were 12 types, sericite FSE, mica MJ-V, talc JA-46R, titanium dioxide CR-50, Yellow LL-100P, Red R-516P, Black BL-100P, Powder La Vie, synthetic fluorine phlogopite PDM-9WB, mica titanium TIMIRON SUPER RED, silica beads and Excel Mica. The coating amount was the same as in the foregoing Example. Thus, 12 types of the coated powders were obtained.

The coated powders of the invention as obtained above and the coated powders of Comparative Examples which were treated in the ordinary manner were evaluated by the following test methods.

(Verification of a Skin Care Effect)

The skin care effect referred to in the invention means an effect of providing a moisturizing effect and maintaining a smooth skin. This effect was verified by the following method.

Test method: A 10% sodium laurylsulfate solution was applied on the bent side of the forearm and covered for each of 30 panelists having healthy skin, for 2 hours to prepare a rough skin model. As a applied sample, a mixture of vaseline (Nikko Rika K.K.) and a coated powder at a ratio of 1:1% by weight was formed. As a comparative sample, a powder before coating in each Example was used as an uncoated powder in the test. Further, as a blank, vaseline alone was applied. A applying site of 2 cm×4 cm was arranged on the rough skin portion, and the sample was applied in a condition of 2 mg/cm$^2$. This procedure was conducted twice a day in the morning and in the evening, and continued for 5 days. A moisture content of keratin on the skin was measured using SKICON-200 (I. B. S. K.K.). As the moisturizing effect, a ratio of low frequency conductivity before applying and low frequency conductivity after 5 days from applying was obtained in terms of a relative conductivity calculated as described below. Further, the rough skin was caused by disorder of the skin top and the skin groove. The smooth feeling or the rough feeling on the surface of the skin was evaluated by panelists themselves. The evaluation standard was scored in the following manner to obtain a total value.

Relative conductivity=Low frequency conductivity after applying/Low frequency conductivity before applying×100(%)

improved—+1 unchanged—0 worsened—−1

(Verification of an Anti-aging Effect)

Active oxygen generated by external stimulation with ultraviolet rays and chemical substances or by drying or like acts, to change the dermis matrix through decrease of collagen, increasing denaturation of elastin or the like to lose an elasticity of the skin. The anti-aging effect of the invention refers to an effect of restoring the elasticity of the skin by improving the conditions of the connective tissues. This effect was verified by the following method.

Test method: With respect to a test site of the skin care effect, a ratio of elasticity (relative elasticity) of the skin before applying and elasticity of the skin after 5 days from applying was measured using a cutometer (Cutometer SEM 474 manufactured by COURAGEKHAZAKA electronic GmbH). The relative elasticity was obtained by the following formula to obtain an average.

Relative elasticity=Elasticity after applying/Elasticity before applying×100 (%)

With respect to the coated powders and the uncoated powders produced in Examples 2 to 5 and Comparative Examples 1 to 3, the skin care effect (relative conductivity and improved condition of rough skin) was shown in Table 1, and the anti-aging effect (relative elasticity) in Table 2.

TABLE 1

|  | Coated powder | | Uncoated powder | |
|---|---|---|---|---|
|  | Relative conductivity | Condition of rough skin | Relative conductivity | Condition of rough skin |
| Mica in Example 2 | 135% | +21 | 100% | 0 |
| Powder La Vie in Example 2 | 137% | +19 | 103% | 0 |
| Mica titanium in Example 2 | 135% | +20 | 95% | −6 |
| Excel Mica in Example 2 | 137% | +25 | 100% | 0 |
| Synthetic fluorine phlogopite in Example 3 | 135% | +25 | 100% | +2 |
| Finely divided titanium dioxide in Example 4 | 133% | +18 | 93% | −8 |
| Silica beads in Example 5 | 134% | +19 | 92% | −9 |
| Sericite in Example 5 | 138% | +23 | 101% | 0 |
| Talc in Example 5 | 136% | +22 | 102% | 0 |
| Titanium dioxide in Example 5 | 139% | +18 | 99% | −2 |
| Yellow iron oxide in Example 5 | 137% | +19 | 98% | −2 |
| Red iron oxide in Example 5 | 135% | +20 | 97% | −1 |
| Black iron oxide in Example 5 | 133% | +18 | 99% | −5 |
| Synthetic fluorine phlogopite in Comparative Example 1 | 101% | 0 | — | — |
| Synthetic fluorine phlogopite in Comparative Example 2 | 103% | 0 | — | — |
| Sericite in Comparative Example 3 | 100% | +3 | — | — |
| Mica in Comparative Example 3 | 102% | +2 | — | — |
| Talc in Comparative Example 3 | 102% | +3 | — | — |
| Titanium dioxide in Comparative Example 3 | 99% | +1 | — | — |
| Yellow iron oxide in Comparative Example 3 | 100% | 0 | — | — |
| Red iron oxide in Comparative Example 3 | 100% | 0 | — | — |
| Black iron oxide in Comparative Example 3 | 98% | 0 | — | — |
| Powder La Vie in Comparative Example 3 | 102% | 0 | — | — |
| Synthetic fluorine phlogopite in Comparative Example 3 | 102% | +5 | — | — |
| Mica titanium in Comparative Example 3 | 101% | +1 | — | — |
| Silica beads in Comparative Example 3 | 99% | −2 | — | — |
| Excel Mica in Comparative Example 3 | 101% | +2 | — | — |
| applying of vaseline only | 101% | +1 | — | — |

TABLE 2

|  | Relative elasticity | |
|---|---|---|
|  | Coated powder | Uncoated powder |
| Mica in Example 2 | 138% | 98% |
| Powder La Vie in Example 2 | 139% | 103% |
| Mica titanium in Example 2 | 132% | 96% |
| Excel Mica in Example 2 | 130% | 100% |
| Synthetic fluorine phlogopite in Example 3 | 137% | 103% |
| Finely divided titanium dioxide in Example 4 | 137% | 97% |
| Silica beads in Example 5 | 135% | 93% |
| Sericite in Example 5 | 131% | 96% |
| Talc in Example 5 | 139% | 99% |
| Titanium dioxide in Example 5 | 134% | 101% |
| Yellow iron oxide in Example 5 | 133% | 99% |
| Red iron oxide in Example 5 | 138% | 98% |
| Black iron oxide in Example 5 | 138% | 100% |
| Synthetic fluorine phlogopite in Comparative Example 1 | 100% | — |
| Synthetic fluorine phlogopite in Comparative Example 2 | 102% | — |
| Sericite in Comparative Example 3 | 103% | — |
| Mica in Comparative Example 3 | 103% | — |
| Talc in Comparative Example 3 | 101% | — |
| Titanium dioxide in Comparative Example 3 | 100% | — |
| Yellow iron oxide in Comparative Example 3 | 100% | — |
| Red iron oxide in Comparative Example 3 | 101% | — |
| Black iron oxide in Comparative Example 3 | 99% | — |
| Powder La Vie in Comparative Example 3 | 103% | — |
| Synthetic fluorine phlogopite in Comparative Example 3 | 103% | — |
| Mica titanium in Comparative Example 3 | 100% | — |
| Silica beads in Comparative Example 3 | 98% | — |
| Excel Mica in Comparative Example 3 | 101% | — |
| applying of vaseline only | 102% | — |

As is apparent from these results, the coated powders of the invention were found to be excellent in both skin care effect shown by the relative conductivity and the condition of the rough skin in Table 1, and the anti-aging effect shown by the relative elasticity in Table 2.

Subsequently, formulations were formed by incorporating the coated powders of the invention.

Example 6 and Comparative Example 4

(Formation of a Pressed Powder)

Using the coated powders produced in Example 5, a pressed powder shown in Table 3 was formed. For comparison, a product containing the ordinary coated powders produced in Comparative Example 3 was also formed.

TABLE 3

| | Ratio (%) |
|---|---|
| 1. Coated sericite in Example 5 or Comparative Example 3 | 52.00 |
| 2. Coated talc in Example 5 or Comparative Example 3 | 25.00 |
| 3. Coated titanium dioxide in Example 5 or Comparative Example 3 | 8.00 |
| 4. Coated Yellow iron oxide in Example 5 or Comparative Example 3 | 1.25 |
| 5. Coated Red iron oxide in Example 5 or Comparative Example 3 | 0.95 |
| 6. Coated Black iron oxide in Example 5 or Comparative Example 3 | 0.20 |
| 7. Dimethylpolysiloxane (6 cs) | 3.70 |
| 8. Squalane | 2.75 |
| 9. Glyceryl tri-2-ethylhexanoate | 4.05 |
| 10. SEPICIDE HB*[1] | 0.30 |

*[1] Preservative sold by SEPPIC, France.

[Process]

Components 1 to 6 were mixed with a Henschel mixer, and further mixed with a mixture obtained by uniformly mixing components 7 to 10. The resulting mixture was pulverized with an atomizer, passed through a screen, and compressed in a cosmetic pan to obtain a pressed powder.

Example 7 and Comparative Example 5

(Formation of Two-way Powder Foundation)

A two-way powder foundation shown in Table 4 was formed. For comparison, a product containing ordinary coated powders was also formed.

TABLE 4

| | Ratio (%) |
|---|---|
| 1. Coated sericite in Example 5 or Comparative Example 3 | 32.00 |
| 2. Coated Powder La Vie in Example 2 or Comparative Example 3 | 15.00 |
| 3. Coated talc in Example 5 or Comparative Example 3 | 20.00 |
| 4. Coated titanium dioxide in Example 5 or Comparative Example 3 | 9.50 |
| 5. Coated Yellow iron oxide in Example 5 or Comparative Example 3 | 1.60 |
| 6. Coated Red iron oxide in Example 5 or Comparative Example 3 | 0.75 |
| 7. Coated Black iron oxide in Example 5 or Comparative Example 3 | 0.15 |
| 8. Polymethyl methacrylate | 5.0 |
| 9. Zinc stearate | 5.0 |
| 10. Octyldodecyl oleate | 1.50 |
| 11. Squalane | 4.50 |
| 12. Liquid lanolin | 1.50 |
| 13. Glyceryl tri-2-ethylhexanoate | 3.20 |
| 14. SEPICIDE HB | 0.30 |

[Process]

Components 1 to 9 were mixed with a Henschel mixer, and further mixed with a uniform mixture of components 10 to 14. The resulting mixture was pulverized with an atomizer, passed through a screen, and compressed in a cosmetic pan to obtain a two-way foundation.

Example 8 and Comparative Example 6

(Formation of a Powder Eye Shadow)

A powder eye shadow shown in Table 5 was formed. For comparison, a product containing ordinary coated powders was also formed.

TABLE 5

| | Ratio (%) |
|---|---|
| 1. Coated sericite in Example 5 or Comparative Example 3 | 53.40 |
| 2. Coated Excel Mica in Example 2 or Comparative Example 3 | 25.00 |
| 3. Coated mica titanium in Example 5 or Comparative Example 3 | 7.80 |
| 4. Coated silica beads in Example 5 or Comparative Example 3 | 5.50 |
| 5. Coated Yellow iron oxide in Example 5 or Comparative Example 3 | 0.50 |
| 6. Coated Red iron oxide in Example 5 or Comparative Example 3 | 0.35 |
| 7. Coated Black iron oxide in Example 5 or Comparative Example 3 | 0.05 |
| 8. Sorbitan oleate | 1.80 |
| 9. Vaseline | 1.90 |
| 10. Dimethylpolysiloxane | 1.90 |
| 11. Squalane | 1.50 |
| 12. SEPICIDE HB | 0.30 |

[Process]

Components 1 to 7 except mica titanium were mixed with a Henschel mixer, and the mixture was then pulverized with an atomizer. The product was mixed with mica titanium which is component #3, and further mixed uniformly with a uniform mixture of components 8 to 12. The resulting mixture was pulverized with an atomizer, passed through a screen, and compressed in a cosmetic pan to obtain a powder eye shadow.

Example 9 and Comparative Example 7

(Formation of a Lipstick)

A lipstick shown in Table 6 was formed. For comparison, a product containing ordinary coated powders was also formed.

TABLE 6

| | Ratio (%) |
|---|---|
| 1. Coated titanium dioxide in Example 5 or Comparative Example 3 | 1.50 |
| 2. Coated Red iron oxide in Example 5 or Comparative Example 3 | 8.50 |
| 3. Coated silica beads in Example 5 or Comparative Example 3 | 2.25 |
| 4. Red No. 201 | 1.25 |
| 5. Castor oil | 49.20 |
| 6. Octyl dodecanol | 15.50 |
| 7. Beeswax | 7.00 |
| 8. Ozocerite | 5.00 |
| 9. Candelilla wax | 8.00 |
| 10. Carnauba wax | 1.50 |
| 11. Antioxidant | 0.20 |
| 12. SEPICIDE HB | 0.10 |

[Process]

Components 5 to 10 were melted, and uniformly mixed. Components 1 to 4 were added thereto, and the mixture was kneaded with a roll mill, and uniformly dispersed. Subsequently, the dispersion was redissolved, and components 11 and 12 were added thereto. The mixture was poured into a mold, and rapidly cooled. When the product was solidified, the resulting product was withdrawn from the mold, filled in a container, and subjected to flaming for providing the uniform appearance to obtain a lipstick.

Example 10 and Comparative Example 8

(Formation of a Liquid Foundation)

A liquid foundation shown in Table 7 was formed. For comparison, a product containing ordinary coated powders was also formed.

TABLE 7

| | Ratio (%) |
|---|---|
| 1. Coated Powder La Vie in Example 5 or Comparative Example 3 | 7.50 |
| 2. Coated talc in Example 5 or Comparative Example 3 | 2.50 |
| 3. Coated titanium dioxide in Example 5 or Comparative Example 3 | 5.60 |
| 4. Coated Yellow iron oxide in Example 5 or Comparative Example 3 | 1.25 |
| 5. Coated Red iron oxide in Example 5 or Comparative Example 3 | 0.85 |
| 6. Coated Black iron oxide in Example 5 or Comparative Example 3 | 0.15 |
| 7. Decamethyltetrapentanesiloxane | 25.0 |
| 8. Dimethylpolysiloxane (6 cs) | 5.00 |
| 9. Dimethylpolysiloxane·polyoxyalkylene copolymer | 3.80 |
| 10. Propylene glycol | 3.50 |
| 11. Ethanol | 8.00 |
| 12. Purified water | 36.55 |
| 13. SEPICIDE HB | 0.30 |

[Process]

Components 1 to 9 were uniformly mixed. Components 10 to 13 were uniformly mixed and dissolved. While the aqueous layer components were stirred, the oil layer components were added for emulsification to obtain a liquid foundation.

Example 11 and Comparative Example 9

(Formulation of a Creamy Foundation)

A creamy foundation shown in Table 8 was formed. For comparison, a product containing ordinary coated powders was also formed.

TABLE 8

| | Ratio (%) |
|---|---|
| 1. Coated Powder La Vie in Example 5 or Comparative Example 3 | 10.50 |
| 2. Coated talc in Example 5 or Comparative Example 3 | 35.85 |
| 3. Coated silica beads in Example 5 or Comparative Example 3 | 3.50 |
| 4. Coated titanium dioxide in Example 5 or Comparative Example 3 | 8.60 |
| 5. Coated Yellow iron oxide in Example 5 or Comparative Example 3 | 1.25 |
| 6. Coated Red iron oxide in Example 5 or Comparative Example 3 | 0.85 |
| 7. Coated Black iron oxide in Example 5 or Comparative Example 3 | 0.15 |
| 8. Decamethyltetrapentanesiloxane | 5.00 |
| 9. Dimethylpolysiloxane (6 cs) | 4.50 |
| 10. Squalane | 10.50 |
| 11. Isononyl isononanoate | 6.50 |
| 12. Ceresine | 6.00 |
| 13. Carnauba wax | 6.50 |
| 13. SEPICIDE HB | 0.30 |

[Process]

Components 8 to 14 were melted, and uniformly mixed. Components 1 to 7 were added, and uniformly mixed and dispersed. The dispersion was poured into a mold, and cooled to obtain a creamy foundation.

Example 12 and Comparative Example 10

(Formation of an Emulsion)

An emulsion shown in Table 9 was formed. For comparison, a product containing ordinary coated powders was also formed.

TABLE 9

| | Ratio (%) |
|---|---|
| 1. Coated synthetic fluorine phlogopite in Example 3 or Comparative Example 1 | 3.50 |
| 2. Coated silica beads in Example 5 or Comparative Example 3 | 1.00 |
| 3. Isopropyl myristate | 3.50 |
| 4. Isotridecyl isononanoate | 5.50 |
| 5. Vegetable squalane | 2.50 |
| 6. Decamethylpentacyclotetrasiloxane | 2.25 |
| 7. SIMULGEL EG*[2] | 0.50 |
| 8. Butylene glycol | 5.00 |
| 9. Sodium pyrrolidonecarboxylate | 2.00 |
| 10. Purified water | 73.95 |
| 11. SEPICIDE HB | 0.30 |

*[2]Emulsified thickener sold by SEPPIC, France.

[Process]

Components 1 to 7 were uniformly mixed and dispersed. Components 8 to 11 were uniformly mixed, and the oil layer components were added for emulsification to obtain an emulsion.

Example 13 and Comparative Example 11

(Formation of a Sunscreen Cream)

A sunscreen cream shown in Table 10 was formed. For comparison, a product containing ordinary coated powders was also formed.

TABLE 10

| | Ratio (%) |
|---|---|
| 1. Finely divided titanium dioxide in Example 4 or Comparative Example 3 | 15.0 |
| 2. Coated silica beads in Example 5 or Comparative Example 3 | 2.00 |
| 3. Isostearyl neopentanoate | 5.50 |
| 4. Octyl methoxycinnamate | 5.00 |
| 5. Vegetable squalane | 3.00 |
| 6. Decamethylpentacyclotetrasiloxane | 7.00 |
| 7. SIMULGEL A*[3] | 2.50 |
| 8. Propylene glycol | 5.00 |
| 9. Ethanol | 8.00 |
| 10. Monosodium glutamate | 0.15 |
| 11. Purified water | 46.55 |
| 12. SEPICIDE HB | 0.30 |

*[3]Emulsified thickener sold from SEPPIC, France.

[Process]

Components 1 to 7 were uniformly mixed and dispersed. Components 8 to 12 were uniformly mixed, and the oil layer components were added for emulsification to obtain a sunscreen cream.

Example 14 and Comparative Example 12

(Formation of an Eye Liner)

An eye liner shown in Table 11 was formed. For comparison, a product containing ordinary coated powders was also formed.

TABLE 11

| | Ratio (%) |
|---|---|
| 1. Finely divided Powder La Vie in Example 2 or Comparative Example 3 | 10.00 |
| 2. Coated titanium dioxide in Example 5 or Comparative Example 3 | 3.00 |
| 3. Coated Black iron oxide in Example 5 or Comparative Example 3 | 3.50 |
| 4. Organic bentonite | 0.50 |
| 5. Light liquid isoparaffin | 67.10 |
| 6. Carnauba wax | 4.50 |
| 7. Beeswax | 1.00 |
| 8. Microcrystalline wax | 11.00 |
| 9. Vaseline | 2.00 |
| 10. Antioxidant | 0.20 |
| 11. SEPICIDE HB | 0.20 |

[Process]

Components 1 to 4 and a part of component 5 were uniformly mixed and dispersed. Components 5 to 11 were heat-dissolved therein, and the mixture was kneaded with a roll mill, and heat-dissolved again. The remainder of component 5 was added, and the mixture was cooled while being stirred to obtain an eye liner.

Example 15 and Comparative Example 13

(Formation of an O/W Care Cream)

An O/W care cream shown in Table 12 was formed. For comparison, a product containing ordinary coated powders was also formed.

TABLE 12

| | Ratio (%) |
|---|---|
| 1. Finely divided oxidized Powder La Vie in Example 2 or Comparative Example 3 | 10.00 |
| 2. Coated synthetic fluorine phlogopite in Example 3 or Comparative Example 2 | 3.00 |
| 3. Beeswax | 6.50 |
| 4. Cetanol | 3.50 |
| 5. Hydrogenated lanoline | 8.00 |
| 6. Vegetable squalane | 5.0 |
| 7. Tri-2-ethylhexanoic acid glyceride | 4.00 |
| 8. Lipophilic glycerin monostearate | 2.50 |
| 9. Polyoxyethylenesorbitane monolauric acid ester (20 E.O) | 2.00 |
| 10. Butylene glycol | 5.00 |
| 11. Purified water | 50.1 |
| 12. Antioxidant | 0.20 |
| 13. SEPICIDE HB | 0.20 |

[Process]

Components 1 to 9 were heated at 80° C., and uniformly mixed and dispersed. Components 10 to 13 were heat-dissolved at 80° C. The aqueous layer was added to the oil layer while being stirred for emulsification, and the emulsion was cooled to 30° C. to obtain an O/W care cream.

The products in Examples 6 to 15 were, in comparison with the products in comparative Examples 4 to 13, not only good in feeling in use and spreadability, but also the skin-care effect of moisturizing the skin and maintaining the smooth skin, and the anti-aging effect of restoring the elasticity of the skin were markedly observed therein when continuously applying the same product on the skin. Thus, the cosmetics which were superior to the ordinary products were provided.

"SEPIFEEL ONE" sold by SEPPIC, France, which was used as the coating agent of the invention as described in the Examples above, is disclosed in JP-T-2001-510784 (the term "JP-T" as used herein means a published Japanese translation of a PCT patent application) as follows. A mixture of N-palmitoylproline, N-palmitoylglutamic acid and N-palmitoylsarcosine or its salt is deemed to exhibit a substance P antagonist activity and have an antiinflammatory activity on the skin. This function comes under the concept of the skin-care effect and the anti-aging effect referred to in the invention. Accordingly, the case of incorporating "SEPIFEEL ONE" into the product as an additive and the case of incorporating it into the product as a coated powder were compared.

Example 16 and Comparative Example 14

(Powder Foundation)

A powder foundation shown in Table 13 was formed, and compared with a product of ordinary coated powders. The content of "SEPIFEEL ONE" in each product was 3.0%.

TABLE 13

| | Ratio (%) | |
|---|---|---|
| | Example 16 Incorporation of coated powder in Example | Comparative Example 14 Incorporation of coated powder in Comparative Example 3 |
| 1. Synthetic fluorine phlogopite | 16.00 (Example 3) | same as left |
| 2. Talc | 55.00 (Example 5) | 52.00 |
| 3. Titanium dioxide | 8.50 (Example 5) | same as left |
| 4. Yellow iron oxide | 2.10 (Example 5) | same as left |
| 5. Red iron oxide | 0.90 (Example 5) | same as left |
| 6. Black iron oxide | 0.20 (Example 5) | same as left |
| 7. Silica beads | 8.00 (Example 5) | same as left |
| 8. Liquid paraffin | 1.50 | same as left |
| 9. Octyldodecyl oleate | 3.50 | same as left |
| 10. Jojoba oil | 1.00 | same as left |
| 11. SEPIFEEL ONE | — | 3.00 |
| 12. SEPICIDE HB | 0.30 | same as left |

[Process]

Components 1 to 7 were mixed with a Henschel mixer, and a mixture obtained by uniformly dissolving and mixing components 8 to 12 at 80° C. was added thereto and further mixed therewith. The resulting mixture was pulverized twice with an atomizer, then passed through a sieve, and compressed in a cosmetic pan to obtain a powder foundation.

Example 17 and Comparative Example 15

Oil Foundation

An oil foundation shown in Table 14 was formed, and compared with a product of ordinary coated powders. The content of "SEPIFEEL ONE" in each product was 2.0%.

TABLE 14

|  | Ratio (%) | |
| --- | --- | --- |
|  | Coated powder in Example 2 | Coated powder in Comparative Example 3 |
| 1. Excel Mica | 12.00 | same as left |
| 2. Synthetic fluorine phlogopite | 10.5 | same as left |
| 3. Talc | 18.10 | 16.10 |
| 4. Titanium dioxide | 7.50 | same as left |
| 5. Yellow iron oxide | 1.90 | same as left |
| 6. Red iron oxide | 0.85 | same as left |
| 7. Black iron oxide | 0.15 | same as left |
| 8. Silica beads | 5.00 | same as left |
| 9. Polyethylene/polyprolene copolymer | 4.00 | same as left |
| 10. Carnauba wax | 5.50 | same as left |
| 11. Pentaerythritol rosinate | 6.50 | same as left |
| 12. Cetyl isooctanoate | 12.00 | same as left |
| 13. Propylene glycol dicaprinate | 7.00 | same as left |
| 14. Liquid paraffin | 3.50 | same as left |
| 15. SEPIFEEL ONE | — | 2.00 |
| 16. SEPICIDE HB | 0.30 | same as left |

[Process]

Components 1 to 8 were dispersed and mixed. Components 9 to 16 were heat-dissolved at 110° C. Components 1 to 8 dispersed and mixed were added thereto. The temperature was adjusted to 80° C., and the resulting mixture was filled from a bottom of a cosmetic pan by being melted under pressure to obtain an oil foundation.

With respect to Examples 16 and 17 and Comparative Examples 14 and 15, the skin care effect and the anti-aging effect were tested by the foregoing methods. The results are shown in Table 15.

TABLE 15

|  | Relative conductivity | Condition of rough skin | Relative elasticity |
| --- | --- | --- | --- |
| Powder foundation in Example 16 | 137% | +23 | 126% |
| Powder foundation in Comparative Example 14 | 124% | +11 | 108% |
| Oil foundation in Example 17 | 135% | +21 | 130% |
| Oil foundation in Comparative Example 15 | 120% | +10 | 108% |

From the results of Example 15, it was found that incorporation of "SEPIFEEL ONE" into the foundation in the form of the coated powder of the invention was superior in skin care effect and anti-aging effect compared to incorporation thereof into the foundation as a mere additive.

The meritorious effects of the present invention are summarized as follows.

As stated above, in the powder coated with the mixture (lipoamino acid composition) of the specific acylated amino acid and fatty acid in the invention, when used by being incorporated into cosmetics, the high skin-care effect and anti-aging effect are identified, and the coated powder is quite useful to provide better cosmetics than ordinary products.

It should be noted that other objects, features and aspects of the present invention will become apparent in the entire disclosure and that modifications may be done without departing the gist and scope of the present invention as disclosed herein and claimed as appended herewith.

Also it should be noted that any combination of the disclosed and/or claimed elements, matters and/or items may fall under the modifications aforementioned.

What is claimed is:

1. A coated powder which can be used in cosmetics, said powder being coated with a lipoamino acid composition comprising N-acyl derivatives of amino acids shown in the following (1) to (3) and at least one fatty acid(s) selected from fatty acids having a carbon number of at least 12 and at most 22:
   (1) at least one amino acid selected from proline and hydroxyproline,
   (2) at least one amino acid selected from alanine, glycine and sarcosine, and
   (3) at least one amino acid selected from aspartic acid and glutamic acid.

2. The coated powder as claimed in claim 1, wherein the carbon number of said fatty acid is any from 12 to 18.

3. The coated powder as claimed in claim 1, wherein at least a part of the N-acylamino acids are in the form of a salt.

4. The lipoamino acid composition-coated powder as claimed in claim 1, wherein at least a part of said fatty acid is in the form of a metal salt.

5. The coated powder as claimed in claim 1, wherein the N-acyl group of said N-acylamino acids is a saturated aliphatic carboxylate group having a carbon number of at least 12 and at most 22.

6. The coated powder as claimed in claim 5, wherein the carbon number of said N-acyl group is any from 12 to 18.

7. The coated powder as claimed in claim 1, wherein said amino acid (1) is proline.

8. The coated powder as claimed in claim 1, wherein said amino acid (2) is sarcosine.

9. The coated powder as claimed in claim 1, wherein said amino acid (3) is glutamic acid.

10. The coated powder as claimed in claim 1, wherein said fatty acid is at least one selected from lauric acid, myristic acid, palmitic acid, and stearic acid.

11. The coated powder as claimed in claim 1, wherein said N-acyl group of the N-acylamino acids is a palmitoyl group.

12. The coated powder as claimed in claim 1, wherein said lipoamino acid composition comprises from 25 to 70% by weight of the N-acyl derivative(s) of said amino acid (1), from 5 to 50% by weight of the N-acyl derivative(s) of the amino acid (2), from 5 to 25% by weight of the N-acyl derivative(s) of the amino acid (3) and from 5 to 50% by weight of said fatty acid.

13. A cosmetic comprising the coated powder as claimed in any one of claims 1 to 12 in an amount of 0.1% by weight or more.

* * * * *